(12) United States Patent
Pecherer

(10) Patent No.: US 7,736,304 B2
(45) Date of Patent: Jun. 15, 2010

(54) METAL LARYNGOSCOPE BLADE

(75) Inventor: Eugeny Pecherer, Netanya (IL)

(73) Assignee: Truphatek International Ltd. (IL)

( * ) Notice: Subject to any disclaimer, the term of this patent is extended or adjusted under 35 U.S.C. 154(b) by 988 days.

(21) Appl. No.: 10/588,060

(22) PCT Filed: Feb. 29, 2004

(86) PCT No.: PCT/IL2004/000195

§ 371 (c)(1),
(2), (4) Date: Aug. 1, 2006

(87) PCT Pub. No.: WO2005/082231

PCT Pub. Date: Sep. 9, 2005

(65) Prior Publication Data

US 2007/0129606 A1    Jun. 7, 2007

(51) Int. Cl.
*A61B 1/267* (2006.01)
*A61B 1/06* (2006.01)
(52) U.S. Cl. .................. 600/197; 600/185; 600/198
(58) Field of Classification Search ......... 600/185–200; D24/137
See application file for complete search history.

(56) References Cited

U.S. PATENT DOCUMENTS

| 3,426,749 A | 2/1969 | Jephcott |
| 3,598,113 A | 8/1971 | Moore |
| 3,766,909 A | 10/1973 | Ozbey |
| 3,826,248 A | 7/1974 | Gobels |
| 3,856,001 A * | 12/1974 | Phillips ................ 600/194 |
| 4,037,588 A | 7/1977 | Heckele |
| 4,406,280 A | 9/1983 | Upsher |
| 4,437,458 A * | 3/1984 | Upsher ................ 600/193 |
| 4,527,553 A * | 7/1985 | Upsher ................ 600/188 |
| 4,557,256 A | 12/1985 | Bauman |
| 4,565,187 A | 1/1986 | Soloway |
| 4,570,614 A | 2/1986 | Bauman |
| 4,579,108 A | 4/1986 | Bauman |
| 4,583,527 A | 4/1986 | Musicant et al. |
| 4,596,239 A | 6/1986 | Bauman |
| 4,679,547 A | 7/1987 | Bauman |
| 4,878,486 A | 11/1989 | Slater |
| 4,884,558 A | 12/1989 | Gorski et al. |
| 4,924,855 A * | 5/1990 | Salerno et al. ........... 600/199 |
| 4,930,495 A | 6/1990 | Upsher |
| 4,958,624 A | 9/1990 | Stone et al. |

(Continued)

FOREIGN PATENT DOCUMENTS

DE         26 21 232        11/1977

(Continued)

OTHER PUBLICATIONS

Hilbro brochure, Green System Fiber Optic Laryngoscope, Interchangeable Light Guide Insert, Oct. 2001.

(Continued)

*Primary Examiner*—Linda C Dvorak
*Assistant Examiner*—Tina Nguyen
(74) *Attorney, Agent, or Firm*—Hershkovitz & Associates, LLC

(57) ABSTRACT

A metal laryngoscope blade with a resiliently elastically deformable metal blade hook-on fitting for removable double snap engagement into an operative intubation position on a laryngoscope handle with a correspondingly sized handle hook-on fitting.

12 Claims, 5 Drawing Sheets

U.S. PATENT DOCUMENTS

| | | |
|---|---|---|
| 5,060,633 A | 10/1991 | Gibson |
| 5,065,738 A | 11/1991 | Van Dam |
| 5,178,131 A | 1/1993 | Upsher |
| 5,355,870 A | 10/1994 | Lacy |
| 5,529,570 A * | 6/1996 | Storz .......................... 600/199 |
| 5,651,760 A | 7/1997 | Upsher |
| 5,702,351 A | 12/1997 | Bar-Or et al. |
| 5,776,053 A * | 7/1998 | Dragisic et al. ............. 600/195 |
| 5,879,304 A | 3/1999 | Shuchman et al. |
| 6,013,026 A * | 1/2000 | Krauter et al. .............. 600/193 |
| 6,139,491 A | 10/2000 | Heine et al. |
| 6,213,937 B1 | 4/2001 | Vivenzio |
| 6,719,688 B2 | 4/2004 | Pecherer et al. |
| 7,128,710 B1 | 10/2006 | Cranton et al. |
| 2004/0215062 A1 | 10/2004 | Dalle et al. |
| 2005/0234303 A1 * | 10/2005 | McMorrow ................. 600/189 |

FOREIGN PATENT DOCUMENTS

DE    202 18 560    7/2003

OTHER PUBLICATIONS

Medizintechnik KaWe Germany, Laryngoscopes, Megalight F.O.

* cited by examiner

METAL LARYNGOSCOPE BLADE

CROSS-REFERENCE TO RELATED APPLICATIONS

This application is the United States National Stage filing of PCT Application PCT/I12004/000195 having an international filing date of Feb. 29, 2004.

FIELD OF THE INVENTION

The invention is in the field of laryngoscope blades.

BACKGROUND OF THE INVENTION

ISO 7376 standardizes a removable double snap engagement of a metal or plastic laryngoscope blade into an operative intubation position on a laryngoscope handle. Metal laryngoscopes blades include pre-loaded ball bearing mechanisms for effecting the engagement whilst their plastic counterparts have resiliently elastically deformable blade hook-on fittings for effecting same. Metal laryngoscopes blades engage a laryngoscope handle more securely than their plastic counterparts but they are more expensive and therefore cost considerations militate against the former particularly for disposable single use laryngoscope blades. Exemplary laryngoscopes are illustrated and described in inter alia U.S. Pat. No. 4,557,256, U.S. Pat. No. 4,570,614, U.S. Pat. No. 4,958,624, U.S. Pat. No. 5,529,570, U.S. Pat. No. 6,139,491, and U.S. Pat. No. 6,213,937.

SUMMARY OF THE INVENTION

The present invention is for a novel metal laryngoscope blade with a resiliently elastically deformable metal blade hook-on fitting for removable double snap engagement into an operative intubation position on a laryngoscope handle with a correspondingly sized handle hook-on fitting. The present invention can be implemented for an ISO 7376/3 type laryngoscope blade, and both versions of an ISO 7376/1 type laryngoscope blade, namely, the original version with an electric light source disposed toward its leading tip, and the so-called Shucman® version with an electric light source disposed toward its trailing end. The laryngoscope blade is preferably made from stainless steel and is either fashioned as a single discrete item or it can be welded together from two discrete metal parts, namely, a spatula and a blade hook-on fitting. The thickness of the laryngoscope blade and its resiliently elastically deformable metal blade hook-on fitting in particular is selected so as to be, on the one hand, sufficiently sturdy for its intended clinical use and, on the other hand, sufficiently resiliently elastically deformable to effect the intended double snap engagement. The thickness of the laryngoscope blade and its resiliently elastically deformable metal blade hook-on fitting in particular is envisaged to be in the order of 1.2 mm.

BRIEF DESCRIPTION OF THE DRAWINGS

In order to understand the invention and to see how it can be carried out in practice, preferred embodiments will now be described, by way of non-limiting examples only, with reference to the accompanying drawings, in which similar parts are likewise numbered, and in which.

DETAILED DESCRIPTION OF PREFERRED EMBODIMENTS

Figure 1:
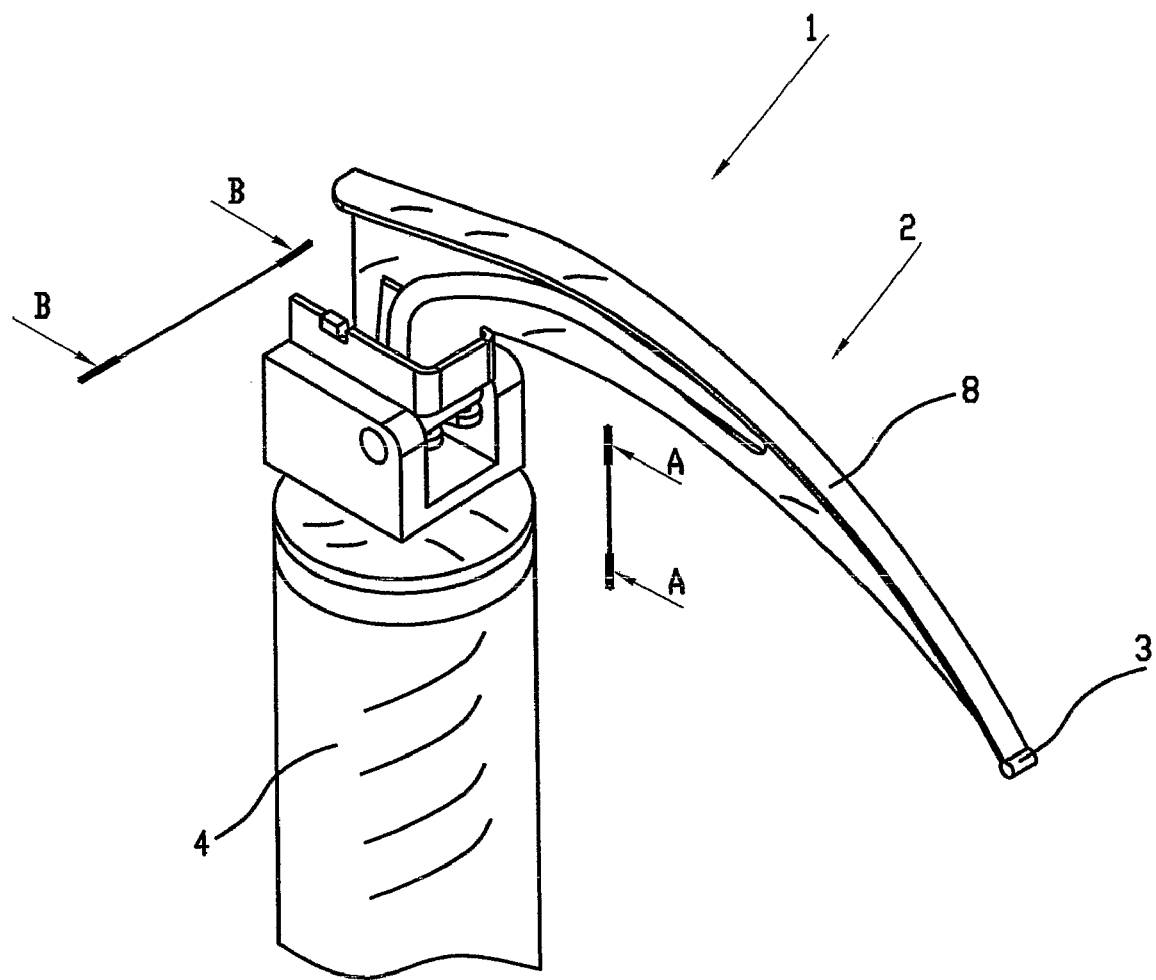
FIG. 1 is a pictorial view of an assembled ISO 7376/3 type laryngoscope with an ISO 7376/3 type laryngoscope blade in accordance with the present invention in its operative intubation position.
Figure 2:
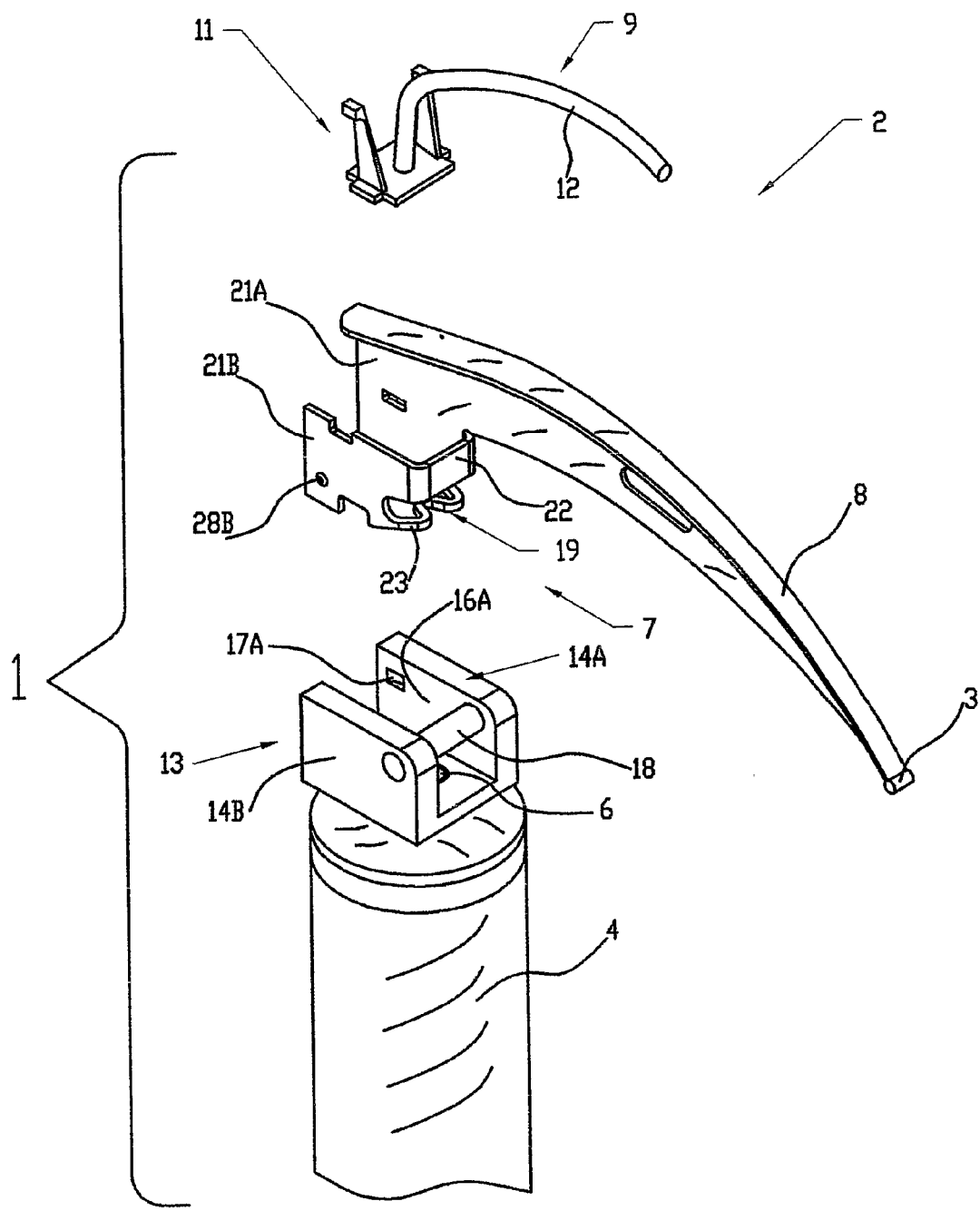
FIG. 2 is an exploded view of the laryngoscope of FIG. 1.

FIGS. 1 and 2 show an ISO 7376/3 type laryngoscope 1 including an ISO 7376/3 type stainless steel laryngoscope blade 2 with a leading tip 3 for removable double snap engagement into an operative intubation position on an ISO 7376/3 type laryngoscope handle 4 having an electrical light source 6 in selective electrical connection with electrical batteries stored therein on depression there toward. The laryngoscope blade 2 includes a resiliently elastically deformable stainless steel blade hook-on fitting 7, and a stainless steel spatula 8 for transversely extending from the laryngoscope handle 4 in its operative intubation position for insertion into a subject's mouth. The laryngoscope blade 2 also includes a L-shaped light guide mount 9 with a trailing connector portion 11 for snap mounting onto the blade hook-on fitting 7 and a light pipe 12 for transferring illumination light from the electrical light source 6 towards a subject's larynx entrance area. The light guide mount 9 is preferably a single discrete item made from acrylic, polycarbonate, or similar light propagating material.

Figure 3:
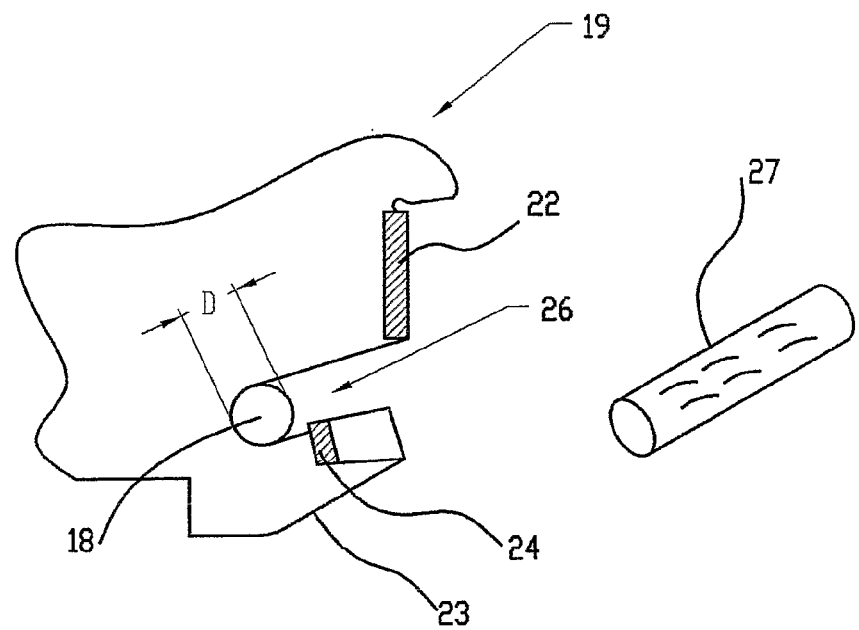
FIG. 3 is a cross sectional view taken along lines A-A in FIG. 1.
Figure 4:
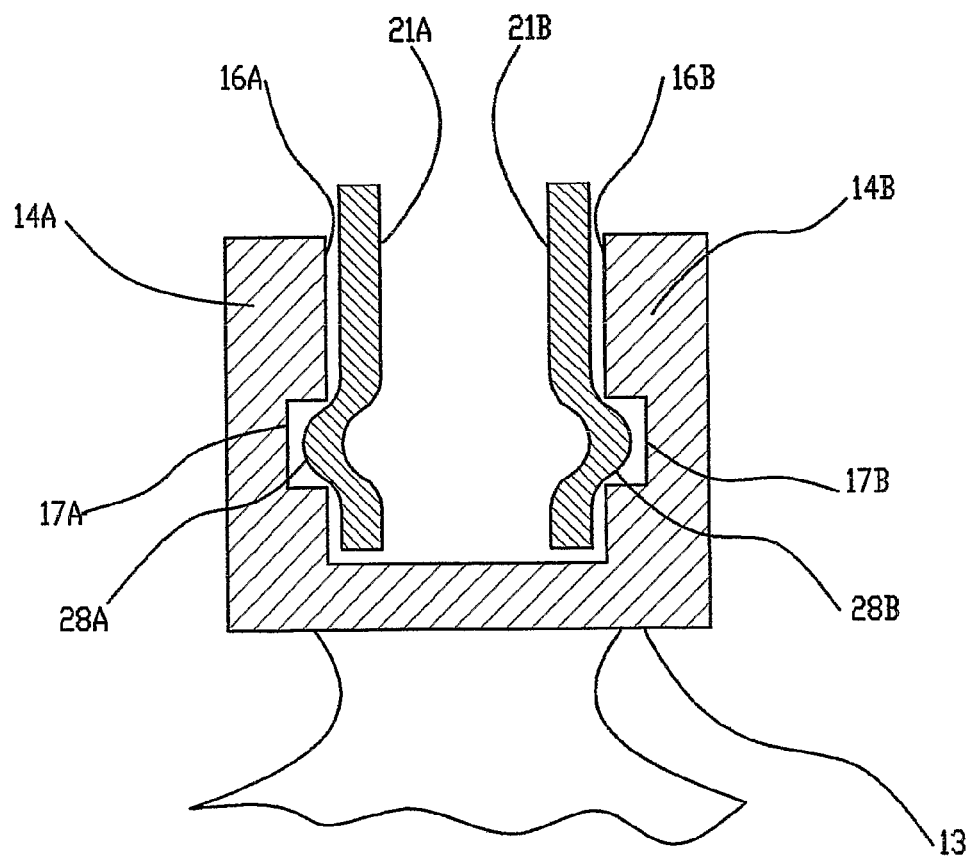
FIG. 4 is a cross sectional view taken along lines B-B in FIG. 1.

The laryngoscope handle 4 has an upright U-shaped handle hook-on fitting 13 with a pair of spaced apart substantially parallel upright supports 14A and 14B with interior surfaces 16A and 16B (see FIG. 4) having a pair of opposite recesses 17A and 17B (see FIG. 4), and a pivot rod 18 extending thereacross. The blade hook-on fitting 7 has a thin walled U-shaped retaining member 19 facing toward the laryngoscope blade's leading tip 3. The retaining member 19 has a pair of spaced apart substantially parallel side walls 21A and 21B, a major front crosspiece 22 extending widthwise between their upper leading portions, and a minor front bridge 23 bridging widthwise between their lowermost leading portions with a centrally disposed indentation 24 directed away from the laryngoscope blade's leading tip 3 whereby the bridge 23 assumes a bifurcated appearance. The retaining member 19 is formed with a leading cutout 26 for snap insertion of the pivot rod 18 therein (see FIG. 3) effected by the pivot rod 18 resiliently downwardly elastically deforming the bridge 23 relative to the crosspiece 22 as it passes over the indentation 24. The indentation 24 prevents the removal of the pivot rod 18 from the cutout 26 without a specific user manipulation of the laryngoscope blade 2 relative to the handle. It should be noted that a simple test for testing the function of the indentation 24 is that it precludes non snap insertion of a GO/NO-GO cylindrical gauge 27 having the same diameter D as the pivot rod 18 into the cutout 26. The side walls 21A and 21B have exterior facing protrusions 28A and 28B disposed towards the trailing end of the laryngoscope blade 2 for snap insertion into a corresponding recess 17 on positive snap manipulation of the blade hook-on fitting 7 fully into the handle hook-on fitting 13 whereupon the laryngoscope blade 2 assumes its operative intubation position (see FIG. 4).

Figure 5:
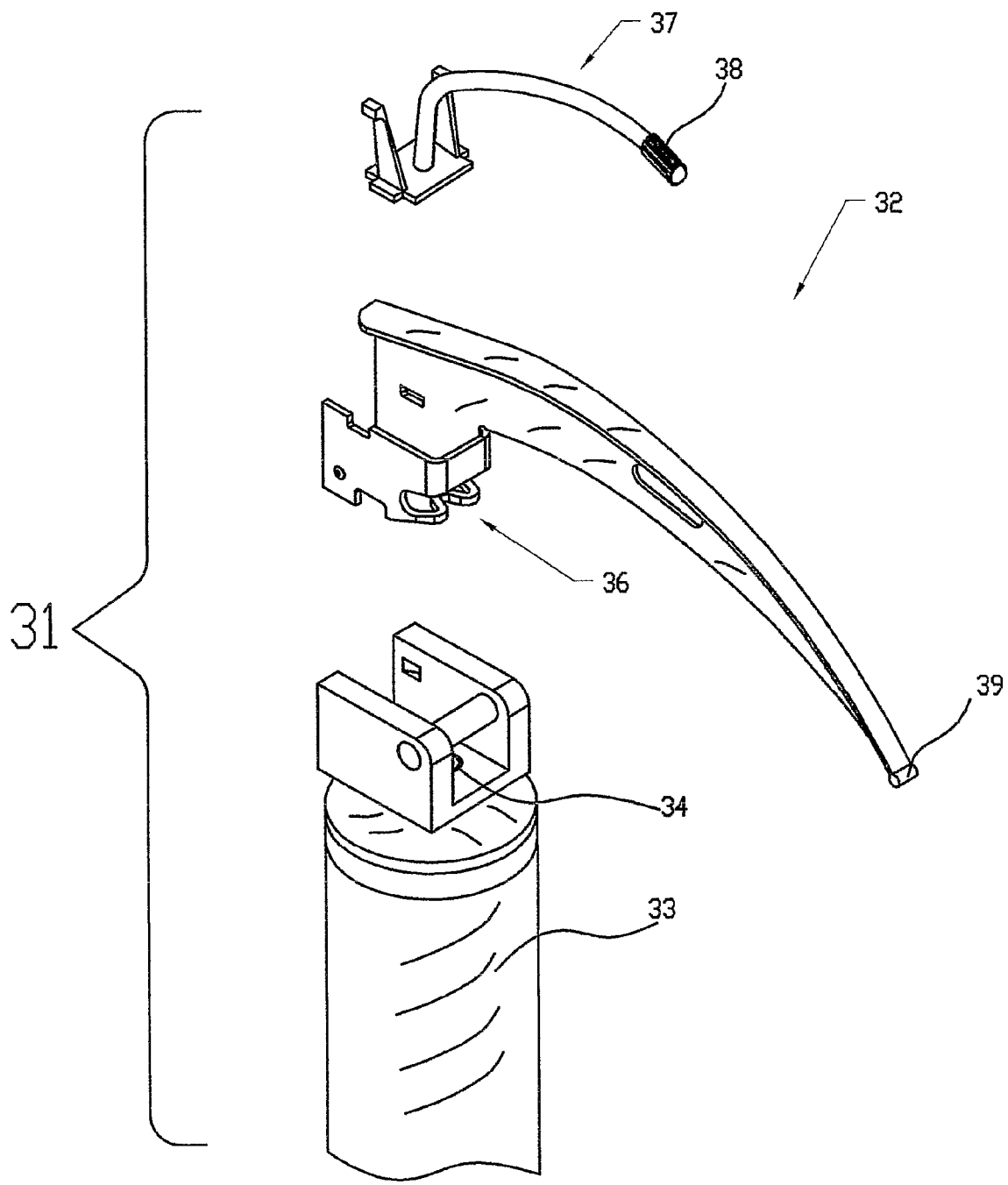
FIG. 5 is an exploded view of an ISO 7376/1 type laryngoscope including the original version of an ISO 7376/1 type laryngoscope blade in accordance with the present invention.

FIG. 5 shows an ISO 7376/1 type laryngoscope 31 including an ISO 7376/1 type stainless steel laryngoscope blade 32 for removable double snap engagement into an operative intubation position on an ISO 7376/1 type laryngoscope handle 33 having an exposed electrical contact 34 in selective electrical connection with electrical batteries stored therein on depression theretoward. The laryngoscope blade 32 has a similar construction to the laryngoscope blade 2 except that it has a different sized blade hook-on fitting 36 and it includes a light guide mount 37 for selectively contacting an electrical light source 38 disposed toward the laryngoscope blade's leading tip 39 with the electrical contact 34 on assembly of the ISO 7376/1 type laryngoscope 31.

Figure 6:
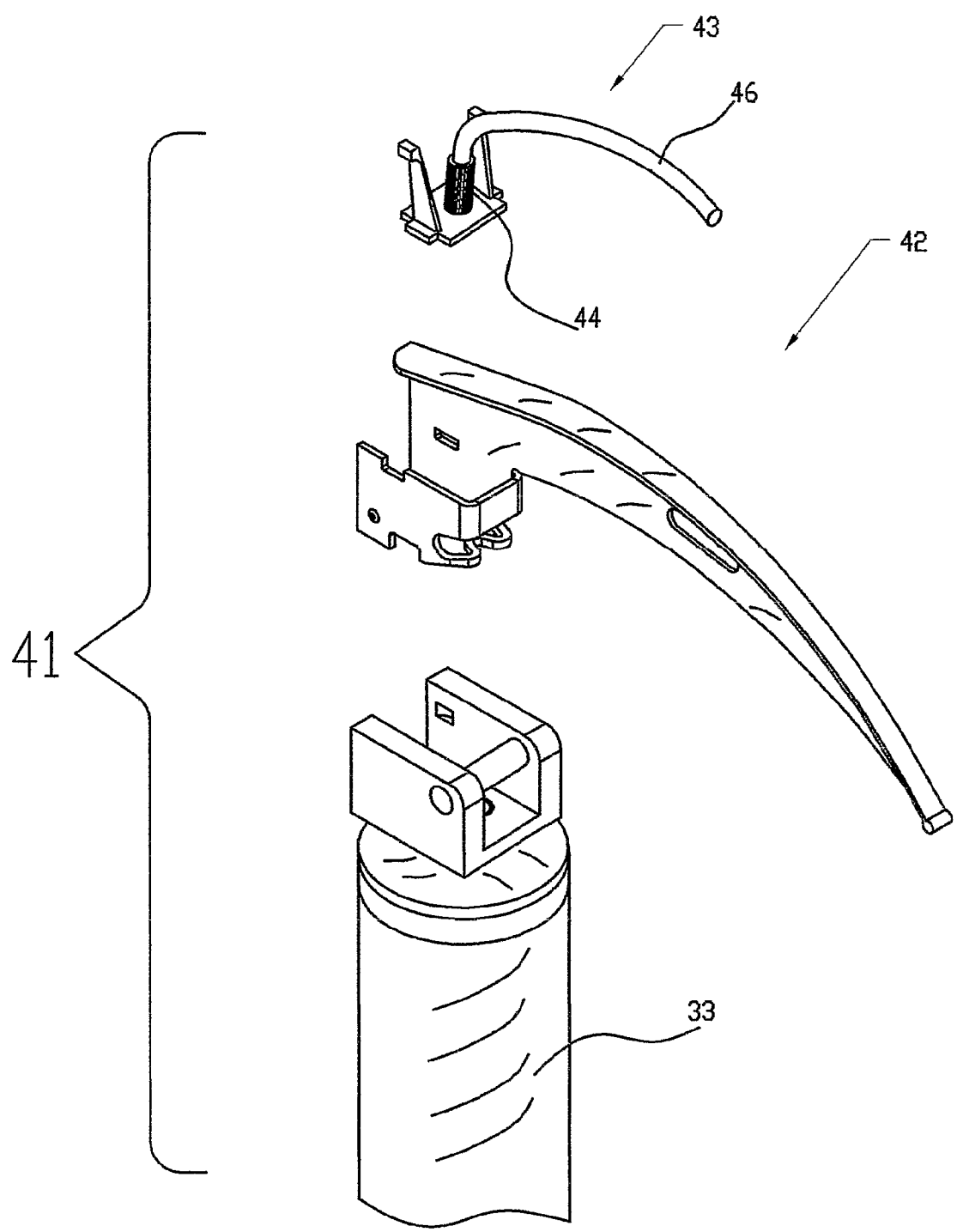
FIG. 6 is an exploded view of an ISO 7376/1 type laryngoscope including the Shucman® version of an ISO 7376/1 type laryngoscope blade in accordance with the present invention.

FIG. 6 shows an ISO 7376/1 type laryngoscope 41 including an ISO 7376/1 type stainless steel laryngoscope blade 42 identical in construction to the ISO 7376/1 type stainless steel laryngoscope blade 32 except that its light guide mount 43 includes an electrical light source 44 disposed toward the laryngoscope blade's trailing end on assembly of the ISO 7376/1 type laryngoscope 41, and a light pipe 46.

While the invention has been described with respect to a limited number of embodiments, it will be appreciated that many variations, modifications, and other applications of the invention can be made within the scope of the appended claims.

The invention claimed is:

1. A metal laryngoscope blade for removable double snap engagement into an operative intubation position on a laryngoscope handle,
   the laryngoscope handle including an upright U-shaped handle hook-on fitting including a pair of spaced apart substantially parallel upright supports with interior surfaces having a pair of substantially opposite recesses, and a pivot rod extending thereacross,
   the metal laryngoscope blade having a leading tip and comprising
   (a) a resiliently elastically deformable metal blade hook-on fitting including a thin walled U-shaped retaining member which includes a pair of spaced apart substantially parallel side wall members providing a gap therebetween and a front crosspiece that extends across the gap and faces toward the metal laryngoscope blades leading tip, and a resiliently elastically deformable bridge extending widthwise across the gap between their leading lowermost regions for defining a cutout for snap receiving the pivot rod therein on positive snap manipulation of said blade hook-on fitting thereon, said side wall members having trailing regions with respect to said bridge having exterior surfaces at least one thereof being provided with a non-frangible metal protrusion integrally formed therewith for snap insertion into a handle hook-on fitting's recess on positive snap manipulation of the blade hook-on fitting fully into the handle hook-on fitting whereupon the laryngoscope blade assumes its operative intubation position, and
   (b) a metal spatula attached to said blade hook-on fitting for transversely extending from the laryngoscope handle in the laryngoscope blade's operative intubation position for insertion into a subjects mouth.

2. The blade as claimed in claim 1 wherein said bridge has a centrally disposed indentation directed away from its leading tip for precluding non snap insertion of a GO/NO-GO cylindrical gauge having the same diameter as said pivot rod into said cutout.

3. The blade as claimed in claim 1 wherein said side wall members have exterior surfaces each provided with a protrusion for snap insertion into a handle hook-on fitting's recess on positive snap manipulation of said blade hook-on fitting fully into the handle hook-on fitting whereupon the laryngoscope blade assumes its operative intubation position.

4. The blade as claimed in claim 1 wherein said blade is constituted by a metal spatula welded onto a metal blade hook-on fitting.

5. A metal ISO 7376/3 type laryngoscope blade as claimed in claim 1 and further comprising a light guide mount for transferring in its operative intubation position illumination light from an electrical light source housed in an ISO 7376/3 type laryngoscope handle toward a subject's larynx entrance area.

6. A metal ISO 7376/1 type laryngoscope blade as claimed in claim 1 and further comprising a light guide mount with an electrical light source disposed toward its leading tip for electrical connection with an electrical power source housed in an ISO 7376/1 type laryngoscope handle in its operative intubation position for providing illumination light for illuminating a subject's larynx entrance area.

7. A metal ISO 7376/1 type laryngoscope blade as claimed in claim 1 and further comprising a light guide mount with an electrical light source disposed toward its trailing end for electrical connection with an electrical power source housed in an ISO 7376/1 type laryngoscope handle in its operative intubation position for providing illumination light for illuminating a subject's larynx entrance area.

8. A light guide mount for mounting onto a blade hook-on fitting of a metal laryngoscope blade as claimed in claim 1 for providing illumination light for illuminating a subject's larynx entrance area in the operative intubation position of the metal laryngoscope blade on a laryngoscope handle.

9. The light guide mount as claimed in claim 8 and including a light pipe for transferring illumination light from an electrical light source housed in an ISO 7376/3 type laryngoscope handle toward a subject's larynx entrance area.

10. The light guide mount as claimed in claim 8 and including an electrical light source positionable toward the leading tip of an ISO 7376/1 type metal laryngoscope blade on mounting the light guide mount thereon for electrical connection with an electrical power source housed in an ISO 7376/1 type laryngoscope handle in the operative intubation position of the ISO 7376/1 type metal laryngoscope blade for providing illumination light for illuminating a subject's larynx entrance area.

11. The light guide mount as claimed in claim 8 and comprising an electrical light source positionable toward the trailing end of said metal laryngoscope blade on mounting the light guide mount thereon for electrical connection with an electrical power source housed in an ISO 7376/1 type laryngoscope handle in the operative intubation position of the ISO 7376/1 type metal laryngoscope blade for providing illumination light for illuminating a subject's larynx entrance area.

12. A metal laryngoscope blade as claimed in claim 1 and further comprising a light guide mount for transferring in its operative intubation position illumination light toward a subject's larynx entrance area, said light guide mount comprising an L-shaped member having a small portion with an end section, and a large portion with an end section, the large portion end section directing the illumination light toward the subjects larynx entrance area when the laryngoscope blade is in an operative intubation position; and
   a connector portion to which said small portion end section is mounted, said connector portion being snap mountable onto said blade hook-on fitting.

* * * * *